Aug. 24, 1948. H. J. SYMONDS Plant Pat. 805
CARNATION PLANT
Filed March 28, 1947
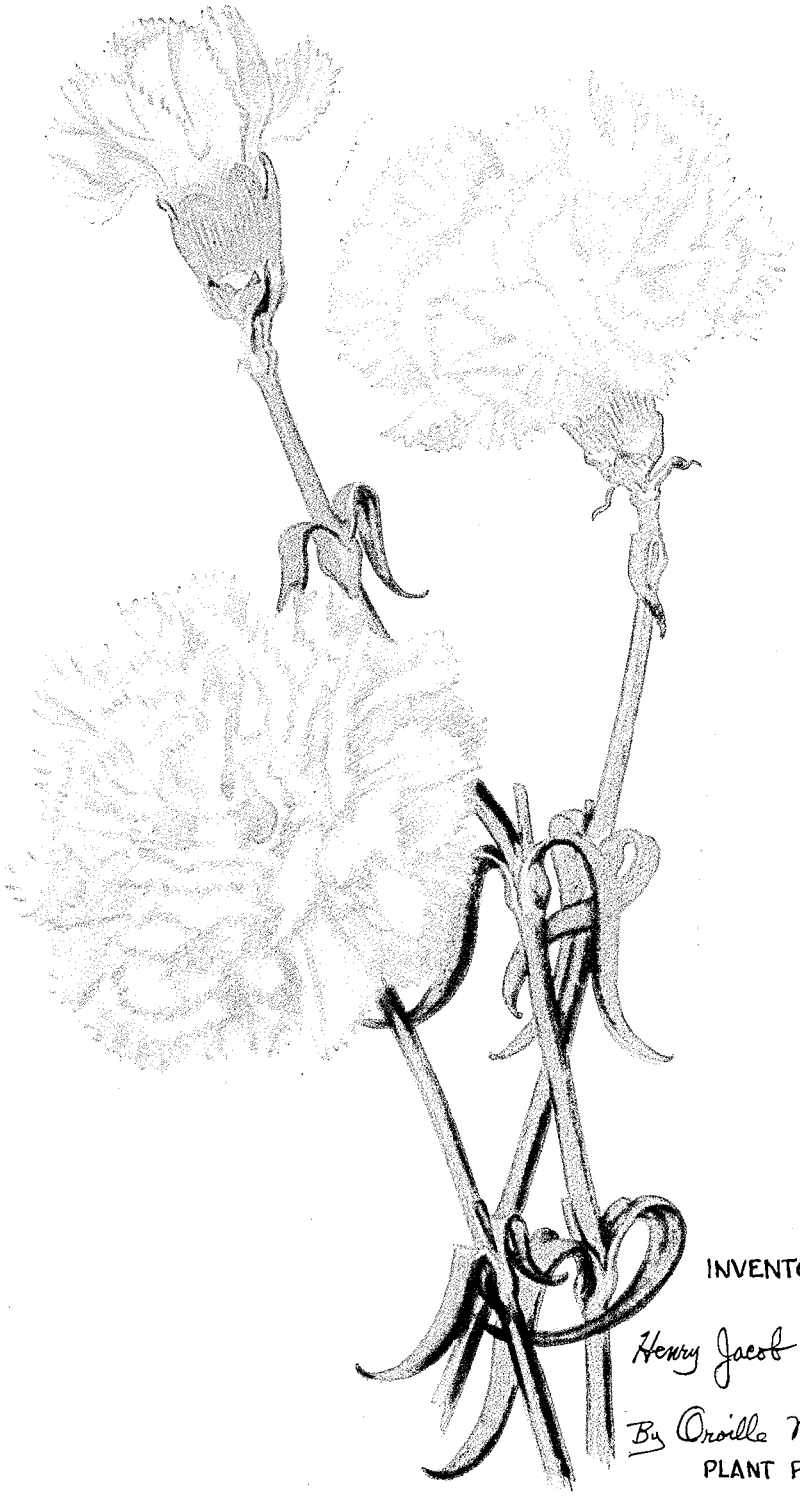
INVENTOR
Henry Jacob Symonds
By Oroille M. Kile
PLANT PATENT AGENT Patented Aug. 24, 1948

Plant Pat. 805

UNITED STATES PATENT OFFICE

805

CARNATION PLANT

Henry Jacob Symonds, Decorah, Iowa

Application March 28, 1947, Serial No. 737,822

1 Claim. (Cl. 47—60)

My present invention relates to an improvement in carnation plants of the greenhouse forcing type. This variety originated from a cross between the varieties King Cardinal (Plant Patent 148) and Matchless (unpatented). It has many of the qualities of the King Cardinal, one of its parents, but its flowers are of an entirely different color. The flowers are a very striking bright and lively rose red color and might commonly be called vivid cerise.

The variety has been reproduced by cuttings, through several generations, and its novel characteristics have proved to be firmly fixed. The accompanying illustrations show a partly opened bud, an opening flower, and a fully opened flower, together with a portion of the stems and foliage—all somewhat enlarged in the original and in as true colors as possible with the medium of water colors.

Following is a detailed description of my new variety. Color plate references are to Ridgway's Color Standards and Nomenclature, but where no plate references are given the ordinary dictionary term is intended.

*The plant*

Flowering habits: Very prolific producer of good quality flowers.

Growth habits: Grows to a height of 3½ feet. Is quite grassy, forming many side shoots. Roots easily.

Health: Resistant to usual carnation diseases.

Foliage:

*Quantity.*—Average.

*Color.*—Approximately Varley's Green (Plate XVIII), covered with heavy gray bloom.

*Size.*—Medium.

*Habit.*—Curling.

Stems: Very long, approximately 30 inches in length. Slender but stout, holding the large flowers erect. Internodes relatively short; nodes small. Color same as foliage.

*The flower*

Bud:

*Size.*—Large. When color begins to show, the average measurement is 1⅜ inches long and 1½ inches in circumference.

*Form.*—Long and pointed.

*Color.*—Between Rose Red (Plate XII) and Tyrian Rose (Plate XII).

*Calyx.*—Very tough and non-splitting; broad, measuring approximately 1 inch across at top. Consists usually of five lobes joined into a single tube. Lobes are bulged at the tips. Color is approximately Bice Green (Plate XVII) with fine vertical stripes of gray.

Flower:

*Size.*—Large, measuring about 3½ inches in diameter.

*Form.*—Full-petaled and regular. Because of the large size of the inner petals, the flower is unusually high-centered.

*Petalage.*—Average is 35 to 40 petals in the month of March.

*Color.*—The general effect is of an all-over color, very bright and lively but very difficult to describe. Ridgway's Color Standards and Nomenclature does not show the color but it would lie somewhere between Rose Red and Tyrian Rose (Plate XII). The color changes as the flower ages and ultimately becomes approximately a true Rose Color (Plate XII).

*Fragance.*—Slight.

*Longevity.*—Excellent, especially as a cut flower.

Petals:

*Shape.*—Outer petals almost round; slightly wavy. Edges shallowly notched. Inner petals are almost as large as outer ones but much more crinkled and folded.

*Color.*—Edges are Rose Color to Tyrian Rose (Plate XII); central portion approximately Rose Red (Plate XII). Very bright.

*Aspect.*—Silky.

*Substance.*—Heavy.

*Arrangement.*—Outer petals almost at right angles to stem, making frame for inner petals which are arranged irregularly and in folded effect.

Reproductive organs:

*Pistil.*—Usually single but sometimes double. White with faint pink tinge. Curved but not curled. About 1¼ inches long. Does not protrude beyond petals at any stage and is never evident in the flower.

*Stamens.*—Few; ragged; white and without anthers. Shorter than pistils.

Having thus disclosed my invention, I claim:

The new and distinct variety of carnation plant substantially as herein shown and described, characterized particularly by its healthy and vigorous growth, its prolific production of flowers, its long, slender but strong stems, its non-splitting calyx, and the novelty and permanency of the bright Rose Red to Tyrian Rose color of its large, high-centered flowers.

HENRY JACOB SYMONDS.